United States Patent
Rubinstein et al.

(10) Patent No.: US 9,050,011 B2
(45) Date of Patent: Jun. 9, 2015

(54) REMOVAL OF ARTIFACTS FROM MAP DATA

(71) Applicant: BIOSENSE WEBSTER (ISRAEL), LTD., Yokneam (IL)

(72) Inventors: Vladimir Rubinstein, Haifa (IL); Meir Bar-Tal, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 175 days.

(21) Appl. No.: 13/726,719

(22) Filed: Dec. 26, 2012

(65) Prior Publication Data

US 2014/0176531 A1    Jun. 26, 2014

(51) Int. Cl.
 G06K 9/00    (2006.01)
 A61B 5/042   (2006.01)
 G06T 19/00   (2011.01)
 A61B 5/06    (2006.01)

(52) U.S. Cl.
 CPC .............. *A61B 5/0422* (2013.01); *A61B 5/042* (2013.01); *A61B 5/062* (2013.01); *A61B 5/068* (2013.01); *G06T 19/00* (2013.01); *G06T 2210/41* (2013.01)

(58) Field of Classification Search
 None
 See application file for complete search history.

(56) References Cited

U.S. PATENT DOCUMENTS

| 7,095,890 B2 * | 8/2006 | Paragios et al. ............... 382/173 |
| 7,515,954 B2 | 4/2009 | Harlev |
| 2006/0094951 A1 * | 5/2006 | Dean et al. .................... 600/407 |
| 2007/0299352 A1 | 12/2007 | Harlev |
| 2009/0069704 A1 | 3/2009 | MacAdam |
| 2009/0112109 A1 | 4/2009 | Kuklik |
| 2010/0274123 A1 * | 10/2010 | Voth .............................. 600/424 |

FOREIGN PATENT DOCUMENTS

| EP | 1070480 B1 | 9/2006 |
| WO | WO 2007137045 A3 | 4/2008 |
| WO | WO 2008136008 A9 | 12/2008 |

OTHER PUBLICATIONS

Hong et al. "Simple Geodesic Regression for Image Time-Series" University of North Carolina, 2012.*
EP Search Report No. EP 13 19 9453 Dated Feb. 20, 2014.

* cited by examiner

*Primary Examiner* — Jon Chang
*Assistant Examiner* — Oneal R Mistry
(74) *Attorney, Agent, or Firm* — Louis J. Capezzuto (57) ABSTRACT

A method for mapping, consisting of receiving an initial set of measured values of a physiological parameter, which were measured at respective locations in a body organ and receiving a three-dimensional (3D) map of the organ including an array of spatial map elements. The method includes forming a correspondence between the respective locations at which the measured values were measured and a sub-group of the map elements, and in response to the correspondence, associating respective element values of the physiological parameter with map elements other than the sub-group. The method further includes adjusting the respective element values so that contiguous sets of the map elements form a geodesic, and displaying a map of the organ showing the adjusted element values.

26 Claims, 5 Drawing Sheets

REMOVAL OF ARTIFACTS FROM MAP DATA

FIELD OF THE INVENTION

The present invention relates generally to measurements of physical parameters, and specifically to measurements of parameters associated with a body organ such as the heart.

BACKGROUND OF THE INVENTION

In medical procedures, such as mapping the electrical activity of the heart, the measurements are typically relatively noisy. A system to reduce the effect of the noise on the measurements would be beneficial.

SUMMARY OF THE INVENTION

An embodiment of the present invention provides a method for mapping, including:

receiving an initial set of measured values of a physiological parameter, which were measured at respective locations in a body organ;

receiving a three-dimensional (3D) map of the organ comprising an array of spatial map elements;

forming a correspondence between the respective locations at which the measured values were measured and a sub-group of the map elements;

in response to the correspondence, associating respective element values of the physiological parameter with map elements other than the sub-group;

adjusting the respective element values so that contiguous sets of the map elements form a geodesic; and displaying a map of the organ showing the adjusted element values.

In one embodiment the body organ includes a heart, and the physiological parameter consists of a local activation time of the heart.

Typically, the spatial map elements include planar polygons having vertices corresponding to positions on a wall of the body organ. In a disclosed embodiment the planar polygons include triangles, and the sub-group includes respective nearest triangles to the respective locations. The map elements other than the subgroup may include one or more adjacent triangles having a common side with each of the respective nearest triangles.

The method may further include identifying the one or more adjacent triangles in response to a slowness vector associated with each of the respective nearest triangles.

Adjusting the respective element values may include adjusting element values of centroids of a given nearest triangle and of the one or more triangles adjacent to the given nearest triangle to form the geodesic. Alternatively or additionally, adjusting the respective element values may include minimizing localized displacement vectors associated with the centroids.

In an alternative embodiment the map elements other than the subgroup include one or more triangles not having a common side with each of the respective nearest triangles.

In a further alternative embodiment the geodesic includes a spatial geodesic.

In a yet further alternative embodiment displaying the map includes incorporating isochronal lines associated with the organ into the map.

In a further disclosed embodiment the geodesic includes a temporal geodesic.

Receiving the initial set of measured values may include simultaneously receiving a plurality of measured values of the physiological parameter from a plurality of respective electrodes at the respective locations.

There is further provided, according to an embodiment of the present invention, apparatus for mapping, including:

a probe configured to:

generate an initial set of measured values of a physiological parameter, which were measured at respective locations in a body organ, and generate a three-dimensional (3D) map of the organ comprising an array of spatial map elements; and a processor, configured to:

form a correspondence between the respective locations at which the measured values were measured and a sub-group of the map elements, in response to the correspondence, associate respective element values of the physiological parameter with map elements other than the sub-group, adjust the respective element values so that contiguous sets of the map elements form a geodesic, and display a map of the organ showing the adjusted element values.

The present disclosure will be more fully understood from the following detailed description of the embodiments thereof, taken together with the drawings, in which:

DETAILED DESCRIPTION OF EMBODIMENTS

Overview

An embodiment of the present invention provides a method for mapping a physical parameter associated with a body organ. Typically, and as assumed herein, the body organ is the heart of a subject, and the physical parameter comprises local activation times (LATs) associated with the beating of the heart. The LAT is an indication of the flow of electrical activity through walls of the heart, and embodiments of the present invention use an initial set of measured values of the LATs.

A correspondence is formed between the initial set of LATs and a sub-group of spatial map elements, typically polygonal elements in the form of a mesh, of the heart wall. Except where otherwise stated, in the following description the polygonal spatial map elements are assumed to comprise triangular elements. The spatial map elements, including the sub-group, may be generated from measured positions of the heart wall.

Once the correspondence has been performed, LATs associated with map elements other than those of the sub-group, i.e., with triangles apart from the sub-group of triangles, are estimated. The estimated LAT values may be adjusted so that centroids of the triangles associated with the LATs, typically including triangles included in the sub-group, form a geodesic. The geodesic is typically a spatial geodesic, wherein distances are minimized. In some embodiments the geodesic comprises a temporal geodesic, in which case the measured times between LATs of the centroids are minimized. The estimation process typically forms multiple geodesics.

Once the LATs have been adjusted to form the multiple geodesics, the LATs may be sorted to generate isochrones. A map of the heart, typically based on the mesh described above, may be displayed showing the adjusted LATs in the form of isochronal lines.

Adjusting the LATs so that they form a geodesic on a map of the heart wall allows the LATs to be smoothed in relation to positions of sections of the heart wall. The inventors have found that such smoothing gives superior results compared to smoothing by prior art methods.

System Description

Figure 1:
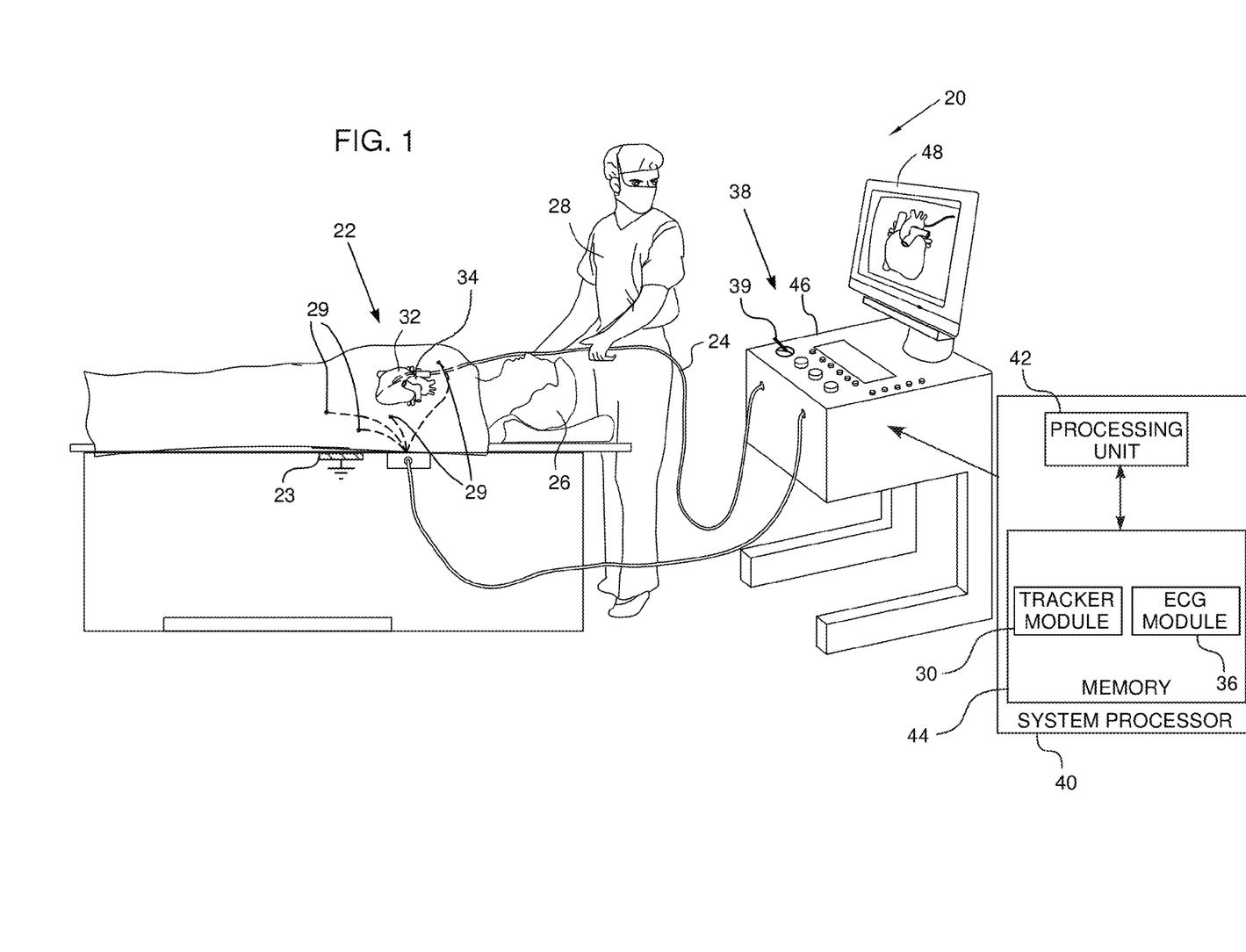
FIG. 1 is a schematic illustration of an electrophysiological signal analysis system, according to an embodiment of the present invention.

Reference is now made to FIG. 1, which is a schematic illustration of an electrophysiological signal analysis system 20, according to an embodiment of the present invention. System 20 may be configured to analyze substantially any physiological parameter or combinations of such parameters, but in the description herein, by way of example, the signals analyzed are assumed to be intra-cardiac electrocardiogram (ECG) potential-time relationships. In order to fully characterize such relationships, the signals need to be referenced in time to each other.

In embodiments of the present invention, the time referencing is accomplished by measuring to an instance in time, herein termed the reference instance, on a reference signal. Herein, by way of example, the reference signal is assumed to comprise a reference ECG potential vs. time signal. Also by way of example, the reference instance is assumed to be the beginning of the QRS complex of the ECG reference signal. For any given location in the heart being mapped, a physical parameter termed a local activation time (LAT) of the electrical activity of the location may be defined in terms of the electrical activity satisfying a predefined condition.

In the following description, the predefined condition is assumed to comprise a time of occurrence of the largest rapid change of potential at the location, and the LAT is assumed to be the time from the reference instance to the following onset of the largest rapid potential deflection at the location. LATs may be positive or negative. Methods for determining the time of occurrence of the largest rapid potential deflection, and other definitions and conditions for determining the LAT, will be familiar to those skilled in the art, and all such methods, definitions, and conditions are assumed to be comprised within the scope of the present invention.

For simplicity and clarity, the following description, except where otherwise stated, assumes an investigative procedure wherein system 20 senses electrical signals from a heart 34, using a probe 24. A distal end 32 of the probe is assumed to have an electrode 22. Those having ordinary skill in the art will be able to adapt the description for multiple probes having one or more electrodes, as well as for signals produced by organs other than a heart.

Typically, probe 24 comprises a catheter which is inserted into the body of a subject 26 during a mapping procedure performed by a user 28 of system 20. In the description herein user 28 is assumed, by way of example, to be a medical professional. During the procedure subject 26 is assumed to be attached to a grounding electrode 23. In addition, electrodes 29 are assumed to be attached to the skin of subject 26, in the region of heart 34.

System 20 may be controlled by a system processor 40, comprising a processing unit 42 communicating with a memory 44. Processor 40 is typically mounted in a console 46, which comprises operating controls 38, typically including a pointing device 39 such as a mouse or trackball, that professional 28 uses to interact with the processor. The processor uses software, including a probe tracker module 30 and an ECG module 36, stored in memory 44, to operate system 20. Results of the operations performed by processor 40 are presented to the professional on a display 48, which typically presents a graphic user interface to the user, a visual representation of the ECG signals sensed by electrodes 22, and/or an image or map of heart 34 while it is being investigated. The software may be downloaded to processor 40 in electronic form, over a network, for example, or it may, alternatively or additionally, be provided and/or stored on non-transitory tangible media, such as magnetic, optical, or electronic memory.

ECG module 36 is coupled to receive electrical signals from electrodes 22 and electrodes 29. The module is configured to analyze the signals and may present the results of the analysis in a standard ECG format, typically a graphical representation moving with time, on display 48.

Probe tracker module 30 tracks sections of probe 24 while the probe is within subject 26. The tracker module typically tracks both the location and orientation of distal end 32 of probe 24, within the heart of subject 26. In some embodiments module 30 tracks other sections of the probe. The tracker module may use any method for tracking probes known in the art. For example, module 30 may operate magnetic field transmitters in the vicinity of the subject, so that magnetic fields from the transmitters interact with tracking coils located in sections of the probe being tracked. The coils interacting with the magnetic fields generate signals which are transmitted to the module, and the module analyzes the signals to determine a location and orientation of the coils. (For simplicity such coils and transmitters are not shown in FIG. 1.) The Carto® system produced by Biosense Webster, of Diamond Bar, Calif., uses such a tracking method. Alternatively or additionally, tracker module 30 may track probe 24 by measuring impedances between electrode 23, electrodes 29 and electrodes 22, as well as the impedances to other electrodes which may be located on the probe. (In this case electrodes 22 and/or electrodes 29 may provide both ECG and tracking signals.) The Carto3® system produced by Biosense Webster uses both magnetic field transmitters and impedance measurements for tracking.

Using tracker module 30 processor 40 is able to measure locations of distal end 32. In addition, using both tracker module 30 and ECG module 36 the processor is able to measure locations of the distal end, as well as LATs of the signals detected at these particular locations. For clarity, in the present disclosure and in the claims, measured locations of the distal end that do not have associated LAT measurements are herein termed non-LAT-locations, and measured locations of the distal end having respective LAT measurements are termed LAT-locations. In embodiments of the present invention, non-LAT-locations are assumed to be used to generate a three-dimensional (3D) anatomic map of walls of heart 34.

Figure 2:
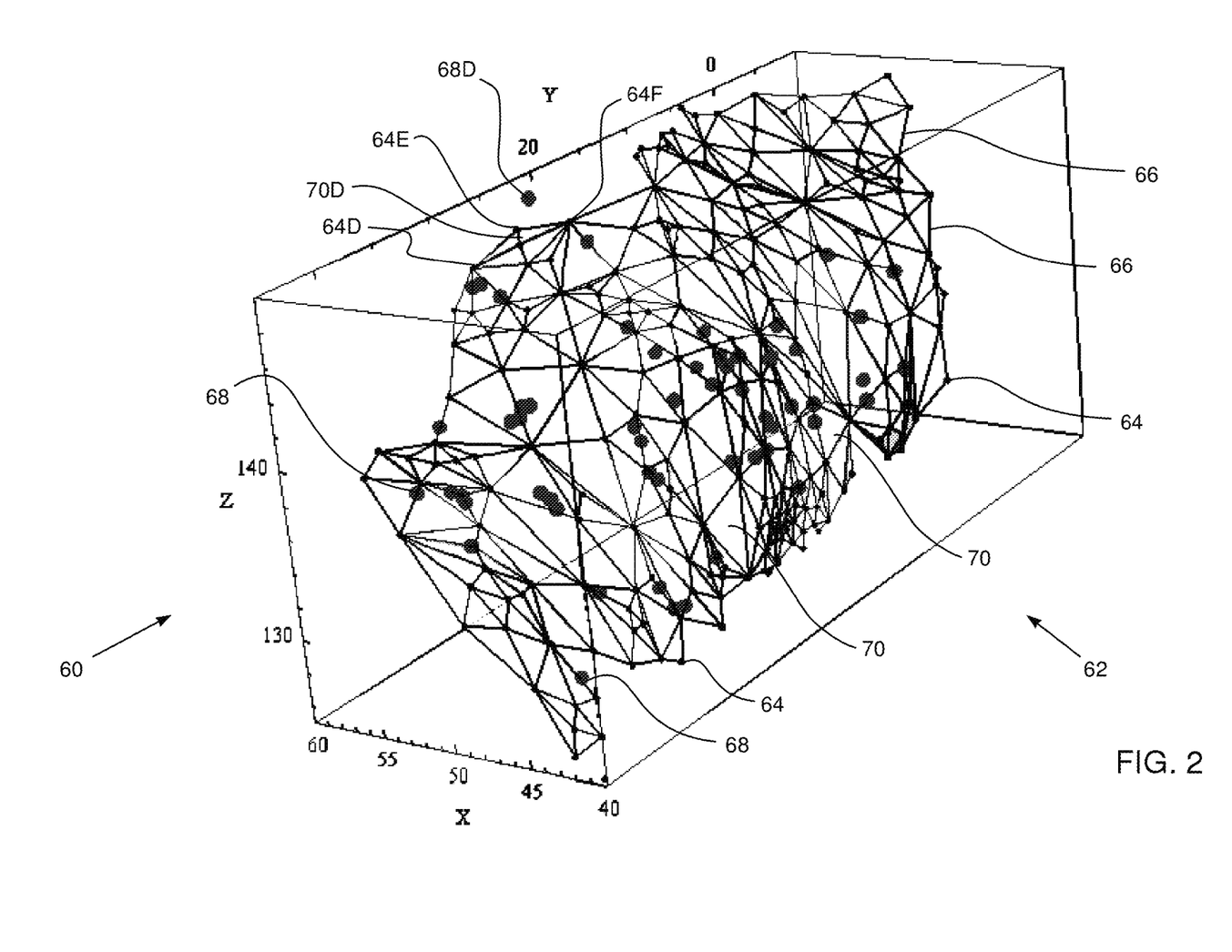
FIG. 2 is a schematic diagram illustrating a three-dimensional map of interior walls of a heart, according to an embodiment of the present invention.

FIG. 2 is a schematic diagram 60 illustrating a 3D map 62 of interior walls of heart 34, as well as LAT-locations, according to an embodiment of the present invention. Diagram 60 may be presented on display 48. For simplicity, only a portion of a complete map is shown in FIG. 2. Map 62 is formulated as a mesh comprising a multitude of non-LAT-location points 64, the positions of which have been evaluated by tracker module 30. The heart wall is moving, but in the evaluation of the positions of the non-LAT-location points, the module allows for such movement, for example by adjusting all measured points to a reference time during a heartbeat, such as the initiation of atrial systole. By methods known in the art, processor 40 connects points 64 by straight inter-point lines 66 so as to form a mesh of connected planar polygons. The planar polygons may have any convenient numbers of sides, and for example may comprise pentagons, or hexagons. For simplicity, in the following description the connected planar polygons are assumed to comprise triangles 70, and those having ordinary skill in the art will be able to adapt the description for the case of planar polygons having other than three sides. Connected triangles 70 form a surface that approximates to the heart interior wall surface.

The diagram also shows LAT-locations 68, each LAT-location having an associated LAT. Typically, LAT-locations and their associated LATs are evaluated at a different time period from the time used by processor 40 to generate map 62. (In presenting diagram 60 on display 48, the value of the LAT associated with a given LAT-location may be indicated by color-coding the dots representing the LAT-locations.) In the present disclosure, and as required, specific non-LAT-locations 64, lines 66, and LAT-locations 68 are distinguished by adding reference letters as a suffix and/or prefix to the identifying numeral. For example, in diagram 60, three non-LAT-locations 64D, 64E, 64F, form a triangle 70D, and an LAT-location 68D is close to, but separate from, triangle 70D.

As for non-LAT-locations, LAT-locations are adjusted to the reference time. In principle, LAT-locations 68 should be in registration with surfaces of triangles 70, since both types of locations, LAT-locations and non-LAT-locations, should lie on the heart wall. In practice, however, the locations are not in registration, due for example, to errors in measurements of the locations, and to errors in adjusting the measured locations. The errors are typically at least partially due to the heart's movement. Embodiments of the present invention correct for the mis-registration of the two types of locations.

Figure 3A:
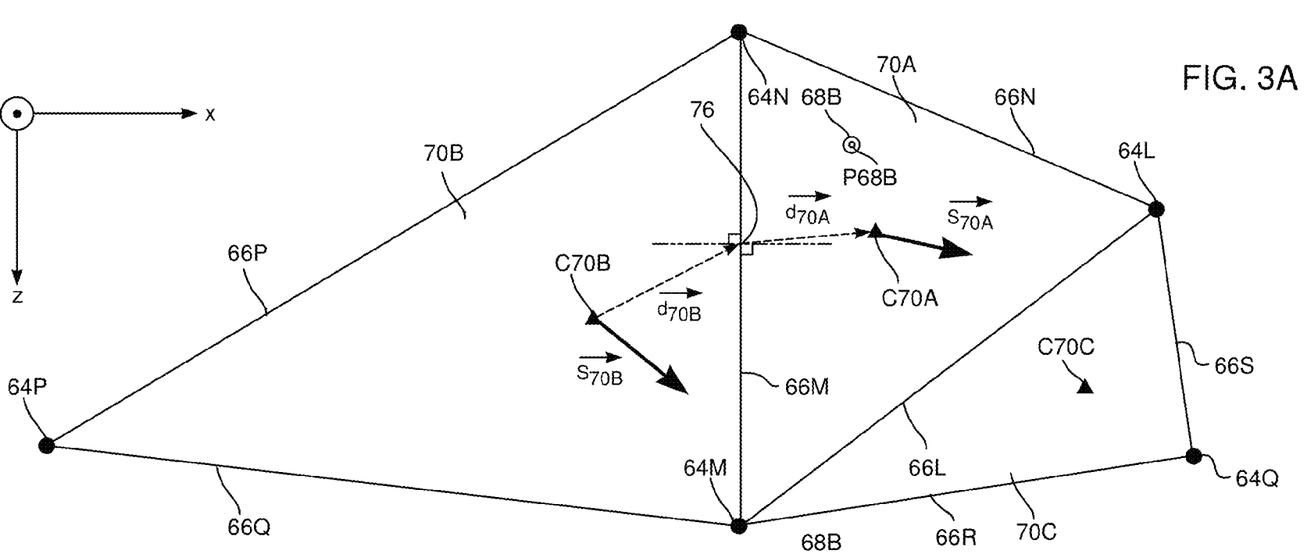
FIGS. 3A and 3B are schematic diagrams of three triangles in the map of FIG. 2, according to an embodiment of the present invention.
Figure 3B:
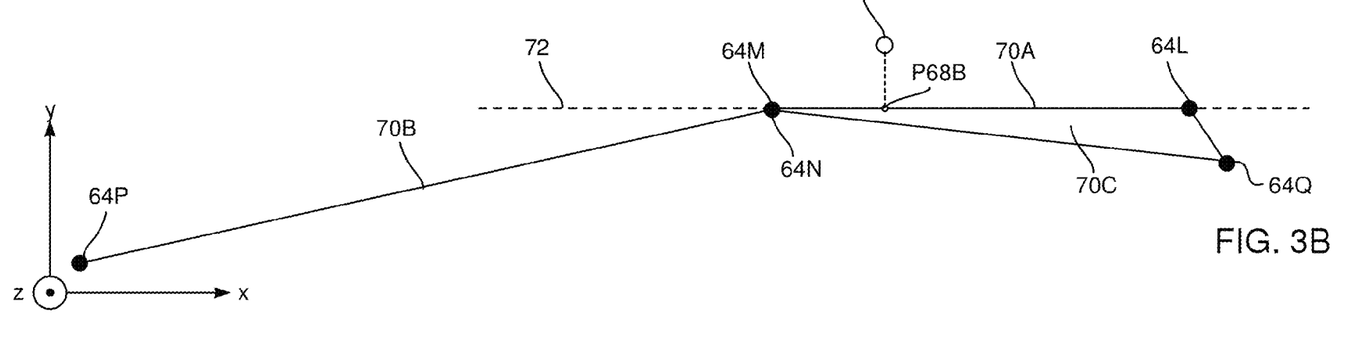

FIGS. 3A and 3B are schematic diagrams of three triangles 70A, 70B, 70C in map 62, according to an embodiment of the present invention. The diagrams are drawn with reference to a set of orthogonal xyz axes, so that FIG. 3B is a side view of the three triangles, and FIG. 3A is a top view. Triangle 70A has as vertices non-LAT-locations 64L, 64M, 64N, the vertices being connected by lines 66L, 66M, 66N. Triangle 70B has as vertices non-LAT-locations 64P, 64M, 64N, connected by lines 66Q, 66M, 66P. Triangle 70C has as vertices non-LAT-locations 64L, 64M, 64Q, connected by lines 66L, 66Q, 66S. Vertices 64M, 64N and line 66M are common to triangles 70A, 70B, and vertices 64M, 64L and line 66L are common to triangles 70A, 70C. By way of example the xyz orthogonal axes are assumed to have the z-axis parallel to line 66M, and to be configured so that triangle 70A lies in a plane 72 parallel to the xz plane. An LAT-location 68B is close to triangle 70A, and is not in plane 72.

Triangle 70A has a geometric centroid C70A, triangle 70B has a geometric centroid C70B, and triangle 70C has a geometric centroid C70C. It will be understood that centroids C70A, C70B, C70C may be calculated from known values of the vertices of respective triangles 70A, 70B, 70C. Other elements of FIGS. 3A and 3B are described below.

The electrical activity of the heart may be thought of as a potential which initiates, at the beginning of every heart beat, at the sinus node, and which flows through the cardiac muscle and connective tissue comprising the heart. At any point on a cavity wall of the heart, an LAT at that point is caused by the potential flowing passed the point. As explained above, mesh 62 approximates to the wall of the heart. Embodiments of the present invention generate estimates of LATs at points on heart cavity walls, using measured LAT-locations and their associated values of LAT, together with measured non-LAT-locations, by estimating flows of the electrical activity through mesh 62, and LATs at centroids of triangles of the mesh, as described below.

Figure 4:
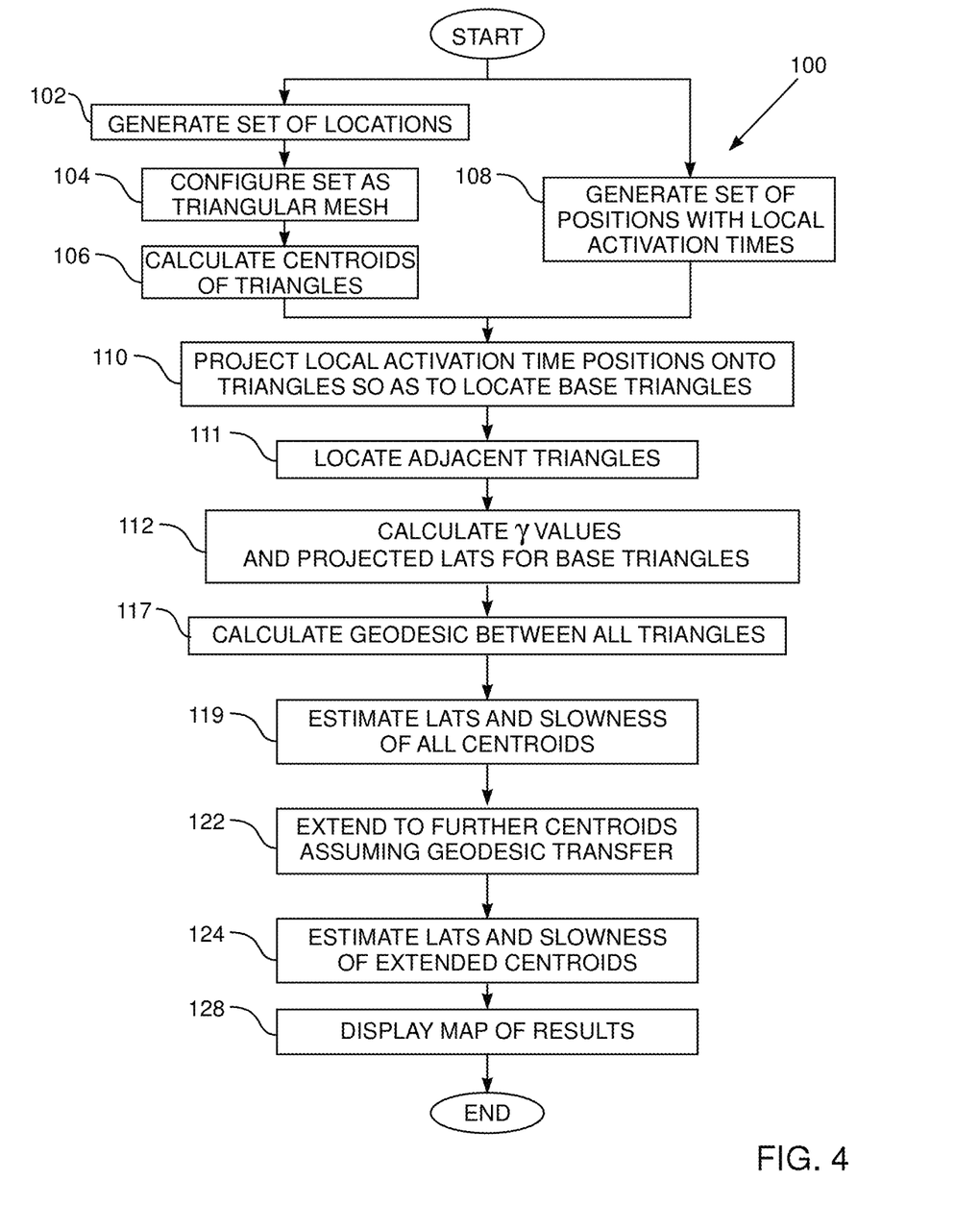
FIG. 4 is a flowchart of steps performed by a processor, in calculating estimated local activation times in a heart, according to an embodiment of the present invention.

FIG. 4 is a flowchart 100 of steps performed by processor 40, in calculating estimated LATs in heart 34, according to an embodiment of the present invention.

In a mapping step 102, the processor and tracker module 30 receive and acquire 3D values of non-LAT-locations 64. The reception and acquisition may be accomplished by moving distal end 32 of probe 24 until the distal end contacts the heart wall.

In a mesh generating step 104, the processor connects non-LAT-locations 64 with straight lines, so as to form mesh 62. Mesh 62 is formed as an array of spatial map elements comprising triangles 70. Methods of forming a mesh of triangular elements from a set of 3D points are known in the art, and typically comprise joining any given point to one or more of its nearest neighbors.

In a centroid step 106, the processor calculates the value of respective centroids of each of the mesh triangles.

In a "raw" LAT step 108, processor 40, using tracker module 30 and ECG module 36, receives and acquires sets of LAT-locations 68, and their associated LATs. The acquisition is substantially similar to the acquisition of non-LAT-locations 64 (step 102), but typically the dwell time of distal end 32 at each LAT-location 68 is longer than the times at non-LAT-locations, to allow the processor to acquire the LAT of the location.

Steps 102 and 108 are independent of each other. Thus, the steps may be performed one after the other, or alternatively they may be performed substantially simultaneously.

In the remaining steps of flowchart 100, the processor performs calculations on substantially all triangles 70 of mesh 62, and on substantially all LAT-locations 68. For clarity, the explanation of the steps refers to triangles 70A, 70B, and 70C of FIGS. 3A and 3B.

In a projection step 110, the processor determines the closest triangle 70 to, i.e., in correspondence with, each LAT-location 68. Such triangles are herein termed base triangles. Once the base triangle for a given LAT-location 68 has been determined, the processor projects the LAT-location onto the base triangle at an LAT-projection point. Thus, referring to FIG. 3A, processor determines that triangle 70A is closest to LAT-location 68B, and so triangle 70A is a base triangle. The processor projects LAT-location 68B to an LAT-projection point P68B on base triangle 70A.

In an adjacent triangle step 111, the processor determines triangles that are adjacent, i.e., contiguous with, the base triangles located in step 110.

In a γ and LAT assignment step 112, for each base triangle element in the mesh, i.e., each triangle having an LAT-projection point, the processor assigns a map element value, herein assumed to comprise a centroidal local activation time, according to equation (1):

$$t_i - \gamma_{ki}\tau_k = \epsilon_t \qquad (1)$$

where t is the assigned local activation time (LAT) of the centroid of the base triangle, i is an identifier of the base triangle, τ is the LAT of the LAT-location, k is an identifier of the LAT-location, $\epsilon_t$ is a constant that is a measure of the similarity of the measured LAT-value ($\tau_k$) and the desired value LAT ($t_i$) in a triangle centroid. $\epsilon_t$ can be preset as a small random value, typically in a range ±(~0.01-0.05) ms, and $\gamma_{ki}$ is a parameter.

This equation will be used in step 119.

The parameter $\gamma_{ki}$ is typically in a range from 0-1, and the value of the parameter may be adjusted, as explained below, by processor 40. Typically, the value of the parameter is set closer to 1 as the distance between the LAT-location and the centroid decreases.

In one embodiment, an exponential function may be used to formulate a pre-set value for parameter $\gamma_{ki}$, according to equation (1a):

$$\gamma_{k,i} = e^{-\alpha \cdot d(i,k)} \tag{1a}$$

where $\alpha$ is a scaling constant, and $d(i,k)$ is a distance between the $i^{th}$ centroid and the $k^{th}$ LAT location.

For the triangles illustrated in FIGS. 3A and 3B, triangle 70A is a base triangle, and equation (1) becomes:

$$t_{70A} = \gamma_{68B,70B} \tau_{68B} \tag{1b}$$

Equation (1) may be considered to be derived from measurements made by a single electrode 22 on probe 24. A more general case (in which equation (1) is included) is the case where LATs are measured simultaneously by M multiple electrodes 22 on probe 24, where M is a positive integer. For such a general case equation (1c) applies:

$$t_{i+m} - \gamma_{ki}^{\Sigma} \cdot (\tau_k + \Delta_{km}) = \epsilon_t \tag{1c}$$

where t, i, $\tau$, $\epsilon_t$, and k are as defined above for equation (1), m is an electrode number, 1≤m≤M, and $\Delta_{km}$ is a time delay of the $m^{th}$ electrode at the $k^{th}$ LAT-location.

In equation (1c), parameter $\gamma_{ki}^{\Sigma}$ is common for all m simultaneously measured points. In an embodiment a value of the parameter $\gamma_{ki}^{\Sigma}$ may be calculated as an average, or as a weighted average, of the individual parameter values given by equation (1d):

$$\gamma_{k,i}[m] = e^{-\alpha \cdot d(i+m,m)} \tag{1d}$$

where $\alpha$ is as defined above for equation (1a), and $d(i+m,m)$ is a distance between the $(i+m)^{th}$ centroid and the $m^{th}$ electrode location for the $k^{th}$ measurement.

For simplicity, the following description assumes that equations (1) and (1a), for the case of measurements being made by a single electrode, apply. Those having ordinary skill in the art will be able to adapt the description for the case covered by equations (1c) and (1d), i.e. for multiple electrodes making measurements simultaneously.

In a geodesic step 117, processor 40 calculates a spatial geodesic Δ between a base triangle centroid and an adjacent triangle centroid. The processor performs this calculation for all triangles in the mesh. The spatial geodesic minimizes the displacement between two centroids, and spatial geodesic Δ may be defined according to equation (2):

$$\Delta = \text{Min}(\vec{d}_i + \vec{d}_j) \tag{2}$$

where $\vec{d}_i$, $\vec{d}_j$ are localized displacement vectors, respectively from the base and adjacent triangle centroids to the line common to the two triangles; the two vectors have a common vertex on the common line.

In the disclosure and in the claims, a geodesic between elements is to be understood as the shortest path between the elements, and a geodesic transfer is the transfer of a parameter along such a path. A geodesic may be a spatial geodesic, in which case the shortest path is the shortest spatial path between the elements. Equation (3) is an example using a spatial geodesic. Alternatively a geodesic may be a temporal geodesic, in which case the shortest path is the shortest temporal path between the elements.

Exemplary localized displacement vectors $\vec{d}_{70A}$, $\vec{d}_{70B}$, between centroids C70B and C70A, are illustrated in FIG. 3A, and have a common vertex 76 on line 66M. (For clarity, the displacement vectors between centroids C70A and C70C, having a common vertex on line 66L, are not drawn in the figure.)

In an LAT and slowness estimation step 119, for all triangles (base and adjacent, i.e., those identified in steps 110, 111), the processor calculates a slowness vector $\vec{S}_1$ to be assigned to respective centroids of the triangles. The slowness value can be defined according to relation (3):

$$\vec{S}_1 = \frac{\vec{V}_j}{|V_i|^2} \tag{3}$$

where $\vec{V}_1$ is an estimated velocity vector, measuring a speed and a direction, of the flow of electrical activity in the $i^{th}$ base triangle.

As is apparent from equation (3), slowness is a vector having a magnitude that is the reciprocal of the speed, and a direction that is the same as the velocity direction.

An exemplary slowness vector $\overrightarrow{S_{70A}}$, connected to centroid C70A, is illustrated in triangle 70A.

In step 119, processor 40 uses equation (4) below to calculate slowness vectors for all triangles.

$$\vec{S}_i - \vec{S}_j = \vec{\epsilon}_S \tag{4}$$

where i is an identifier of one triangle, j is an identifier of a triangle that is bordering triangle i, and $\vec{\epsilon}_S$ is a constant vector that is a measure of the similarity of slowness values of neighboring locations; $|\vec{\epsilon}_S| \geq 0$. Typically, $|\vec{\epsilon}_S|$ approximately 0.01%-1% of the expected value of the slowness.

A value of $\vec{\epsilon}_S$ may be provided to the processor by user 28, and may apply for all mesh 62. In some embodiments, different values of $\epsilon_S$ may be provided typically on the basis of where in relation to elements of the heart triangles i, j are.

$\overrightarrow{S_{70B}}$, connected to centroid C70B, illustrates an exemplary triangle slowness vector.

Also in step 119, for each base triangle, processor uses equation (1) above to calculate the assigned local activation time (LAT) of the centroid of the base triangle The processor calculates activation times to be assigned to the triangle centroids, according to equation (5) below.

$$t_j - t_i = \vec{S}_i \cdot \vec{d}_i + \vec{S}_j \cdot \vec{d}_j \tag{5}$$

where i is an identifier of a pre-cursor triangle, j is an identifier of a triangle bordering pre-cursor triangle i, i.e., a post-cursor triangle, $t_i$, $t_j$ are respective local activation times (LATs) of centroids of the i and j triangles, $\vec{S}_i, \vec{S}_j$ are slowness vectors of the i and j triangles, and $\vec{d}_i, \vec{d}_j$ are generated from equation (2). Inspection of the right side of equation (5) indicates that the first term equals the time of travel of the component of the electrical activity in the pre-cursor triangle, from the common triangle line to the pre-cursor triangle centroid. Similarly, the second term equals the time of travel of the electrical activity in the post-cursor triangle, between the common triangle line and the post-cursor triangle centroid.

Processor 40 applies equation (5) to connect values of $t_j$ and $S_j$, both for the pre-cursor triangle centroid, and for the post-cursor triangle centroid. The application of equation (5) is implemented for all base and conjugate triangles, so generating activation times and slownesses for all triangles determined steps 110 and 111, herein termed a zone of interest.

It will be understood that application of equation (5) assumes a geodesic transfer of electrical activity between all triangle centroids of the zone of interest.

In a continuation step 122, the process of calculating $\vec{d}_i$ is extended by performing the calculation for triangles contiguously surrounding the zone of interest. Each pre-cursor triangle typically has one or more further pre-cursor triangles associated with it, the further pre-cursor triangles forming a contiguous sequence of pre-cursor triangles. The identification of the further pre-cursor triangles may be implemented by analyzing the sides intersected by the slowness vectors.

Similarly, each post-cursor triangle may have one or more further post-cursor triangles associated with it, the further post-cursor triangles also forming a contiguous sequence of post-cursor triangles.

For example, in FIG. 3A, slowness vector $\vec{S}_{70B}$, intersects side 66P, so that there is a further pre-cursor triangle (not shown) having a common side 66P with triangle 70B. Similarly, the slowness vector (not shown) attached to centroid C70C intersects either side 66R or 66S, so there is a further post-cursor triangle, having one of these sides as a common side with triangle 70C.

The two sequences may be considered to start from one base triangle, and all centroids of the triangles in the path formed by the two sequences lie on a spatial geodesic.

In step 122, the processor applies the actions of step 111 to identify further adjacent triangles. As each further adjacent triangle is identified, the processor applies the actions of step 117. The processor continues the generation of adjacent triangles and their activation times until either an edge of mesh 62, or a triangle on another geodesic, is encountered.

The actions up to and including step 122 generate a set of spatial geodesics. Each geodesic comprises a group of contiguous triangles that are connected to form a path taken by the flow of electrical activity being mapped.

Typically, once step 122 has completed, there may remain triangles of mesh 62 that are not on identified geodesics, and so do not have assigned activation times.

In a step 124, the processor calculates activation times and slownesses for adjacent triangles found after implementation of step 122. The activation times and slownesses are calculated by solving the system of equations (4) and (5) for these triangles and using the already determined activation times and slownesses found in step 119 for triangles bordering the zone of interest.

In a final step 128, the processor displays the activation times, and/or the slowness vectors, of the centroids of triangles of mesh 62, on display 48. Typically, the smoothed isochronal lines are incorporated into the display.

By reviewing the description of flowchart 100 it will be understood that equations presented above (equations (1), (4) and (5)) are not independent, and cannot be solved sequentially.

Figure 5:
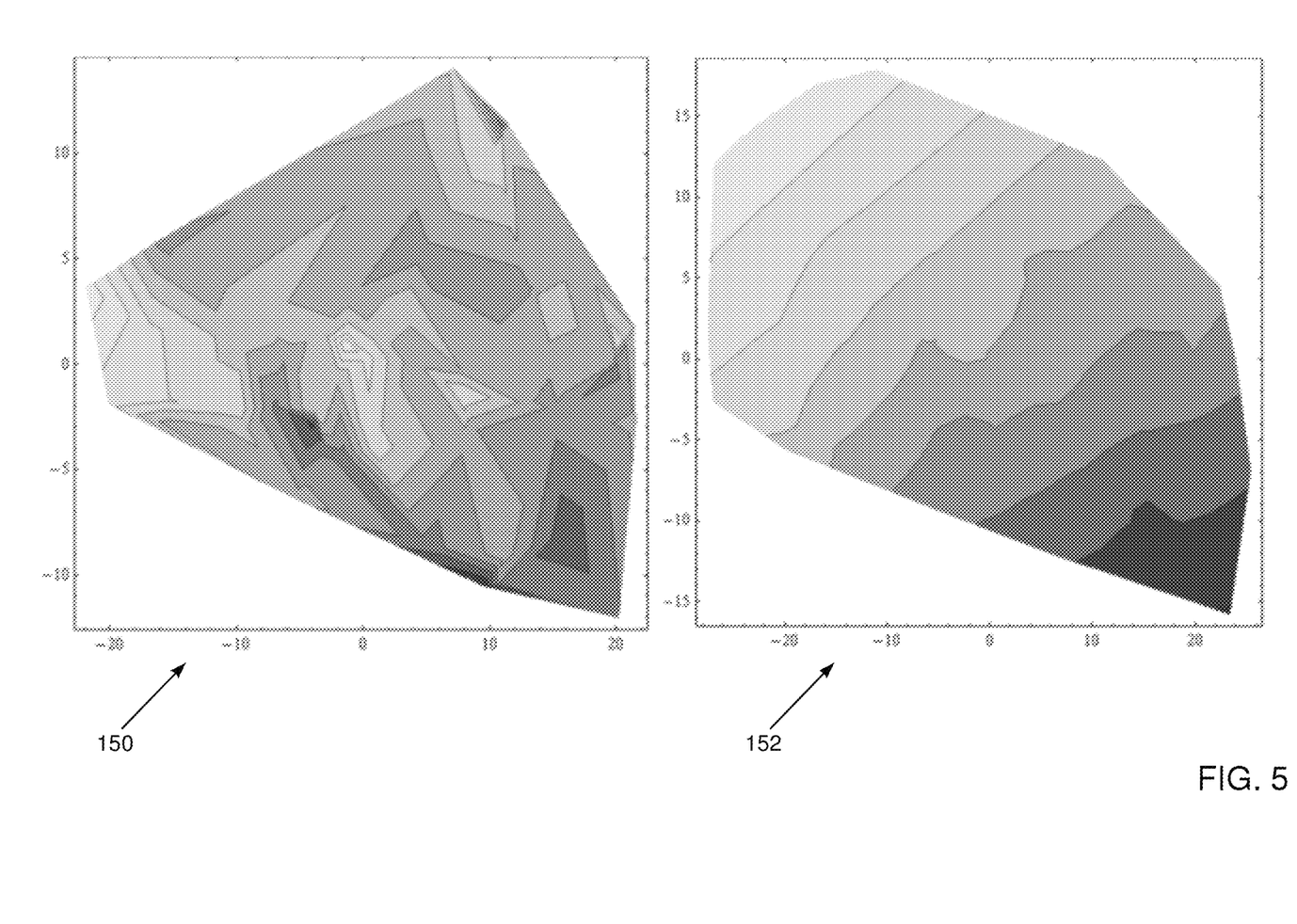
FIG. 5 shows schematic illustrations of isochronal lines, according to an embodiment of the present invention.

FIG. 5 shows schematic illustrations of isochronal lines, according to an embodiment of the present invention. A diagram 150 shows isochronal lines generated from local activation times generated as described above for step 108. The lines are drawn using only the measured LATs, with minimal interpolation and extrapolation. A diagram 152 shows isochronal lines generated according to flowchart 100, as applied to the same LATs used for diagram 150. For clarity, the isochronal lines are separated by different gray levels, indicative of the different times associated with the lines. As is evident from diagram 152, the isochronal lines in diagram 152 are considerably smoother than those of diagram 150.

While the description above has been generally directed to having system 20 analyze and adjust local activation times, it will be understood that the analysis and adjustments described above may be applied to other physiological parameters associated with an organ such as the heart. For example, rather than operating with times, system 20 may be configured to operate with voltages traversing an organ. As another example, there is heat flow during ablation of an organ, and the heat flow through the organ may manifest itself as temperature changes of the organ. System 20 may be configured to analyze and adjust measured temperatures of the organ. Those having ordinary skill in the art will be able to identify other physiological parameters that system 20 is applicable to, such as the infra-red radiation from an organ as it functions, and all such parameters are assumed to be included in the scope of the present invention.

In addition, while the description above has assumed that the geodesic transfer of electrical activity comprises transfer via spatial geodesics, embodiments of the present invention also include transfer via temporal geodesics. Those having ordinary skill in the art will be able to adjust the description, for example by not using equation (3) but rather minimizing equation (5), to accommodate temporal geodesic transfer.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method for mapping, comprising:
   receiving an initial set of measured values of a physiological parameter, which were measured at respective locations in a body organ comprising a heart, wherein the physiological parameter comprises a local activation time of the heart;
   receiving a three-dimensional (3D) map of the heart comprising an array of spatial map elements, the spatial map elements comprising planar polygons comprising triangles having vertices corresponding to positions on a wall of the heart;
   forming a correspondence between the respective locations at which the measured values were measured and a sub-group of the map elements, wherein the sub-group comprises respective nearest triangles to the respective locations;
   in response to the correspondence, associating respective element values of the physiological parameter with map elements other than the sub-group, the map elements other than the sub-group comprising one or more adjacent triangles having a common side with each of the respective nearest triangles, and the one or more adjacent triangles being in response to a slowness vector associated with each of the respective nearest triangles;

adjusting the respective element values so that contiguous sets of the map elements form a geodesic; and displaying a map of the heart showing the adjusted element values.

2. The method according to claim 1, wherein the map elements other than the subgroup comprise one or more triangles not having a common side with each of the respective nearest triangles.

3. The method according to claim 1, wherein the geodesic comprises a spatial geodesic.

4. The method according to claim 1, wherein displaying the map comprises incorporating isochronal lines associated with the organ into the map.

5. The method according to claim 1, wherein the geodesic comprises a temporal geodesic.

6. The method according to claim 1, wherein receiving the initial set of measured values comprises simultaneously receiving a plurality of measured values of the physiological parameter from a plurality of respective electrodes at the respective locations.

7. Apparatus for mapping, comprising:
a probe configured to:
generate an initial set of measured values of a physiological parameter, which were measured at respective locations in a body organ comprising a heart, wherein the physiological parameter comprises a local activation time of the heart, and generate a three-dimensional (3D) map of the organ comprising an array of spatial map elements, wherein the spatial map elements comprise planar polygons comprising triangles having vertices corresponding to positions on a wall of the heart; and a processor, configured to:
form a correspondence between the respective locations at which the measured values were measured and a sub-group of the map elements, wherein the sub-group comprises respective nearest triangles to the respective locations, in response to the correspondence, associate respective element values of the physiological parameter with map elements other than the sub-group, the map elements other than the sub-group comprising one or more adjacent triangles having a common side with each of the respective nearest triangles, and the one or more adjacent triangles being in response to a slowness vector associated with each of the respective nearest triangles, adjust the respective element values so that contiguous sets of the map elements form a geodesic, and display a map of the heart showing the adjusted element values.

8. The apparatus according to claim 7, wherein the map elements other than the subgroup comprise one or more triangles not having a common side with each of the respective nearest triangles.

9. The apparatus according to claim 7, wherein the geodesic comprises a spatial geodesic.

10. The apparatus according to claim 7, wherein displaying the map comprises incorporating isochronal lines associated with the organ into the map.

11. The apparatus according to claim 7, wherein the geodesic comprises a temporal geodesic.

12. The apparatus according to claim 7, wherein the probe comprises a plurality of electrodes which simultaneously receive the initial set of measured values of the physiological parameter from the respective locations.

13. A method for mapping, comprising:
receiving an initial set of measured values of a physiological parameter, which were measured at respective locations in a body organ comprising a heart, wherein the physiological parameter comprises a local activation time of the heart;

receiving a three-dimensional (3D) map of the heart comprising an array of spatial map elements, the spatial map elements comprising planar polygons comprising triangles having vertices corresponding to positions on a wall of the heart;

forming a correspondence between the respective locations at which the measured values were measured and a sub-group of the map elements, wherein the sub-group comprises respective nearest triangles to the respective locations;

in response to the correspondence, associating respective element values of the physiological parameter with map elements other than the sub-group, the map elements other than the sub-group comprising one or more adjacent triangles having a common side with each of the respective nearest triangle;

adjusting the respective element values so that contiguous sets of the map elements form a geodesic by adjusting element values of centroids of a given nearest triangle and of the one or more triangles adjacent to the given nearest triangle to form the geodesic; and displaying a map of the heart showing the adjusted element values.

14. The method according to claim 13, wherein adjusting the respective element values comprises adjusting element values of centroids of a given nearest triangle and of the one or more triangles adjacent to the given nearest triangle to form the geodesic.

15. The method according to claim 14, wherein adjusting the respective element values comprises minimizing localized displacement vectors associated with the centroids.

16. The method according to claim 13, wherein the map elements other than the subgroup comprise one or more triangles not having a common side with each of the respective nearest triangles.

17. The method according to claim 13, wherein the geodesic comprises a spatial geodesic.

18. The method according to claim 13, wherein displaying the map comprises incorporating isochronal lines associated with the organ into the map.

19. The method according to claim 13, wherein the geodesic comprises a temporal geodesic.

20. The method according to claim 13, wherein receiving the initial set of measured values comprises simultaneously receiving a plurality of measured values of the physiological parameter from a plurality of respective electrodes at the respective locations.

21. Apparatus for mapping, comprising:
a probe configured to:
generate an initial set of measured values of a physiological parameter, which were measured at respective locations in a body organ comprising a heart, wherein the physiological parameter comprises a local activation time of the heart, and generate a three-dimensional (3D) map of the organ comprising an array of spatial map elements, wherein the spatial map elements comprise planar polygons comprising triangles having vertices corresponding to positions on a wall of the heart; and a processor, configured to:

form a correspondence between the respective locations at which the measured values were measured and a sub-group of the map elements, wherein the sub-group comprises respective nearest triangles to the respective locations, in response to the correspondence, associate respective element values of the physiological parameter with map elements other than the sub-group, the map elements other than the sub-group comprising one or more adjacent triangles having a common side with each of the respective nearest triangles, adjust the respective element values by adjusting element values of centroids of a given nearest triangle and of the one or more triangles adjacent to the given nearest triangle to form the geodesic so that contiguous sets of the map elements form a geodesic, and display a map of the heart showing the adjusted element values.

22. The apparatus according to claim 21, wherein adjusting the respective element values comprises minimizing localized displacement vectors associated with the centroids.

23. The apparatus according to claim 21, wherein the geodesic comprises a spatial geodesic.

24. The apparatus according to claim 21, wherein displaying the map comprises incorporating isochronal lines associated with the organ into the map.

25. The apparatus according to claim 21, wherein the geodesic comprises a temporal geodesic.

26. The apparatus according to claim 21, wherein the probe comprises a plurality of electrodes which simultaneously receive the initial set of measured values of the physiological parameter from the respective locations.

* * * * *